United States Patent
Beebe et al.

(10) Patent No.: US 11,618,021 B2
(45) Date of Patent: Apr. 4, 2023

(54) VOLUME-FREE REAGENT ADDITION AND EXCLUSION-BASED SAMPLE PREPARATION FOR STREAMLINED MULTI-STEP ASSAYS

(71) Applicant: Wisconsin Alumni Research Foundation, Madison, WI (US)

(72) Inventors: David J. Beebe, Monona, WI (US);
Joshua M. Lang, Madison, WI (US);
Duane S. Juang, Madison, WI (US);
Scott M. Berry, Madison, WI (US);
Tamara S. Rodems, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 278 days.

(21) Appl. No.: 16/912,986

(22) Filed: Jun. 26, 2020

(65) Prior Publication Data
US 2020/0406260 A1 Dec. 31, 2020

Related U.S. Application Data

(60) Provisional application No. 62/868,296, filed on Jun. 28, 2019.

(51) Int. Cl.
*G01N 33/50* (2006.01)
*B01L 3/00* (2006.01)
*G01N 33/543* (2006.01)

(52) U.S. Cl.
CPC ... *B01L 3/502746* (2013.01); *B01L 3/502715* (2013.01); *B01L 3/502784* (2013.01);
(Continued)

(58) Field of Classification Search
CPC ......... B01L 3/502746; B01L 3/502715; B01L 3/502784; B01L 2200/0642;
(Continued)

(56) References Cited

U.S. PATENT DOCUMENTS

2007/0243634 A1  10/2007  Pamula et al.
2011/0114490 A1   5/2011  Pamula et al.
2011/0140706 A1   6/2011  Groves et al.

FOREIGN PATENT DOCUMENTS

WO  2008098236       6/2008
WO  2013006312 A2    1/2013
WO  2013006312 A3    1/2013

OTHER PUBLICATIONS

Yang, Hao, V. N. Luk, M. Abeigawad, I. Barbulovic-Nad and A. R. Wheeler, Anal. Chem., 2009, 81, 1061-1067. (Year: 2009).*

(Continued)

*Primary Examiner* — Christine T Mui
(74) *Attorney, Agent, or Firm* — Boyle Fredrickson, S.C.

(57) ABSTRACT

A method of sample preparation for streamlined multi-step assays is provided. The method includes the step of providing a microfluidic device including a reservoir defined by a surface configured to repel an aqueous solution. A dried reagent is provided on a portion of the surface and the reservoir is filled with an oil. A first droplet formed from the aqueous solution is positioned on the dried reagent so to pick-up and re-dissolve the dried reagent therein so as to expose the portion of the surface. In addition, a second droplet of an aqueous solution may be deposited on a hydrophilic spot patterned on the surface. A magnetic force may be configured to interact magnetically with the paramagnetic beads within the first droplet to move the droplet through the oil in the reservoir or to move the paramagnetic beads from the first droplet, through the oil, into the second droplet.

26 Claims, 6 Drawing Sheets

(52) U.S. Cl.
 CPC ............................ *G01N 33/54326* (2013.01);
  *B01L 2200/0642* (2013.01); *B01L 2200/0673*
  (2013.01); *B01L 2200/16* (2013.01); *B01L*
  *2300/0864* (2013.01); *B01L 2400/043*
  (2013.01)

(58) Field of Classification Search
 CPC ......... B01L 2200/0673; B01L 2200/16; B01L
  2300/0864; B01L 2400/043; G01N
  33/54326
 USPC .................................................. 422/502, 500
 See application file for complete search history.

(56) References Cited

OTHER PUBLICATIONS

S. Newman, A. P. Stephenson, M. Willsey, B. H. Nguyen, C. N. Takahashi, K. Strauss and L. Ceze, Nat. Commun., 2019, 10, 1706. (Year: 2019).*

D. Juang, J. Lang, D. Beebe, Lab Chip, 2022, 22, 286. (Year: 2022).*

Sista, R., Lab Chip, 2008, 8, 2188-2196. (Year: 2008).*

Li, Chao et al., "Exclusive Liquid Repellency: An Open Multi-Liquid-Phase Technology for Rare Cell Culture and Single-Cell Processing", ACS Appl. Mater. Interfaces 2018, 10, 17065-17070.

Li, Chao et al., "Automated system for small-population single-practice processing enabled by exclusive liquid repellency", SLAS Technolgoy, Apr. 24, 2019, vol. 24, No. 6, pp. 535-542.

Berry, S.M., et al., "Using Exclusive-Based Sample Preparation(ESP) to Reduce Viral Load Assay Cost", PLoS one, 2015, vol. 10, No. 12, Aricle No. e0143631, pp. 1-8.

PCT/U2020/040013, International Search Report and Written Opinion, dated Apr. 9, 2021, 8 pages.

A microfluidic device for dry sample preservation in remote settings; Lab on a Chip, vol. 13, No. 22, Jan. 1, 2013, Stefano Begolo et al., pp. 4331-4342, XP055211735, ISSN 1473-0197; the whole document.

* cited by examiner

VOLUME-FREE REAGENT ADDITION AND EXCLUSION-BASED SAMPLE PREPARATION FOR STREAMLINED MULTI-STEP ASSAYS

CROSS-REFERENCE TO RELATED APPLICATION

This application claims benefit from U.S. Provisional Application Ser. No. 62/868,296, filed Jun. 28, 2019, the entirety of which is incorporated herein.

REFERENCE TO GOVERNMENT GRANT

This invention was made with government support under CA81648 awarded by the National Institutes of Health and W81XWH-16-1-0514 awarded by the ARMY/ARO. The government has certain rights in the invention.

FIELD OF THE INVENTION

This invention related generally to microfluidics, and in particular, to a system and method for volume-free reagent addition and exclusion-based sample preparation for streamlined multi-step assays.

BACKGROUND AND SUMMARY OF THE INVENTION

Liquid handling in nearly all assays can be primarily divided into two main categories: 1) adding a reagent into a pre-existing liquid phase (such as adding drugs to cell culture media) in which the target analyte (such as cells) can either be immobilized to a solid surface (adherent cells on the bottom of a dish) or reside in the liquid phase (such as non-adherent cells suspended in media); and 2) solution exchange, in which the target analyte has to be immobilized to a solid surface (such as cells attached to the bottom of a dish or antibodies immobilized to the bottom of an ELISA plate) and the liquid phase is mostly removed and replaced with another liquid phase (for changing solution conditions or washing). Although these operations can usually be performed reliably and with ease using a pipette in traditional macro-scale assays, it becomes much harder, and in many cases impossible, to perform for microscale assays with very small liquid volumes. Further, these operations often yield unreliable and problematic results. For example, in a macroscale assay, addition of 1 microliter (µL) of reagent to 1000 µL of solution only increases the total volume of the solution by approx. 0.1% which usually has little effect in terms of dilution of the original solution. However, adding the same 1 µL of reagent to a 1 µL microscale droplet would double the total volume of the droplet. Hence, any molecules already present in the original solution would be diluted by 50%.

Similarly, when performing a solution exchange, the residual liquid remaining on the solid surface after aspiration accounts for a very small percentage of the total assay volume and is often negligible. However, it becomes a much more significant problem in microscale assays due to the much higher surface to volume ratio. Thus, new strategies that can be utilized to perform reagent addition or a solution exchange without significantly perturbing the final volume of the assay would greatly benefit the field of microscale assays as a whole.

In view of the foregoing, it is a primary object and feature of the present invention to provide a method of a method of sample preparation for streamlined multi-step assays that allows for the volume-free addition of a reagent to a sample.

It is a further object and feature of the present invention to provide a method of sample preparation for streamlined multi-step assays that allows for the preparation of an exclusion-based sample during a solution exchange.

It is a still further object and feature of the present invention to provide a method of sample preparation for streamlined multi-step assays that is simple and inexpensive to practice.

In accordance with the present invention, a method of sample preparation for streamlined multi-step assays is provided. The method includes the step of providing a microfluidic device including a reservoir defined by a surface configured to repel an aqueous solution. A dried reagent is provided on a portion of the surface. The reservoir is filled with an oil and a droplet of the aqueous solution is positioned on the dried reagent. The droplet picks-up and re-dissolves the dried reagent therein so as to expose the portion of the surface.

The step of providing the dried reagent on the portion of the surface includes the additional steps depositing the reagent on the surface and allowing reagent to dry and physically adsorb onto surface. The droplet may include paramagnetic beads therein. The step of positioning the droplet of the aqueous solution on the dried reagent may include the steps of generating a magnetic force and positioning the magnetic force to interact magnetically with the paramagnetic beads within the droplet. The magnetic force is moved to initiate corresponding movement of the droplet to the portion of the surface.

A hydrophilic spot may be patterned on the surface at a second location. The droplet with the dissolved reagent therein may be moved to the hydrophilic spot and pinned at the hydrophilic spot. The step of moving the droplet with the dissolved reagent to the hydrophilic spot may include the additional steps of positioning the magnetic force to interact magnetically with the paramagnetic beads within the droplet and moving the magnetic force to initiate corresponding movement of the droplet to the hydrophilic spot.

The hydrophilic spot may be a first hydrophilic spot and the method may include the additional step of patterning a second hydrophilic spot on the surface at a third location. In addition, the aqueous solution may be a first aqueous solution and the droplet may be a first droplet. A second droplet of a second solution may be pinned at the second hydrophilic spot. The magnetic force may be positioned to interact magnetically with the paramagnetic beads within the first droplet. Movement of the magnetic force may be used to initiate corresponding movement of the paramagnetic beads from the first droplet to the second droplet.

The dried reagent may be a first dried reagent and the portion of the surface may be a first portion. A second dried reagent may be provided on a second portion of the surface. The second dried reagent on the second portion of the surface may be provided by depositing the second reagent on the second portion of the surface and allowing the second reagent to dry and physically adsorb onto the second portion of the surface. The magnetic force may interact magnetically with the paramagnetic beads within the droplet and moved to initiate corresponding movement of the droplet to the second portion of the surface. The second dried reagent may be picked-up and re-dissolved in the droplet so as to expose the second portion of the surface.

In accordance with a further aspect of the present invention, a method of sample preparation for streamlined multi-step assays is provided. The method includes the step of providing a microfluidic device including a reservoir defined by a surface configured to repel aqueous solutions. First and second hydrophilic spots are patterned at corresponding first and second locations of the surface. The reservoir is filled with an oil. A first droplet of a first aqueous solution is deposited on the first hydrophilic spot and a second droplet of a second aqueous solution is deposited on the second hydrophilic spot. The first droplet includes paramagnetic beads. The first droplet may be pinned at the first hydrophilic spot and the second droplet may be pinned at the second hydrophilic spot. A magnetic force is generated and configured to interact magnetically with the paramagnetic beads within the first droplet. The magnetic force is moved to initiate corresponding movement of the paramagnetic beads from the first droplet, through the oil, into the second droplet.

A dried reagent may be provided at a third location the surface prior to filling the reservoir with oil. The step of providing the dried reagent on the portion of the surface may include the additional steps depositing the reagent in a third aqueous solution on the surface and allowing the third aqueous solution to dry such that a dried reagent is physically adsorbed onto surface. A third droplet of a third aqueous solution may be positioned on the dried reagent. The third droplet picking-up and re-dissolving the dried reagent therein so as to expose the portion of the surface. The paramagnetic beads may be initially in the third droplet and the method may include the additional steps of positioning the magnetic force to interact magnetically with the paramagnetic beads within the third droplet and moving the magnetic force to initiate corresponding movement of the paramagnetic beads from the third droplet, through the oil, into the first droplet. Alternatively, the magnetic force may be moved to initiate corresponding movement of the third droplet into fluid communication with the first droplet. It is further contemplated with the paramagnetic bead with the second droplet to position the magnetic force to interact magnetically with the paramagnetic beads within the second droplet and move the magnetic force to initiate corresponding movement of the paramagnetic beads from the second droplet, through the oil, into the third droplet. Thereafter, the magnetic force may interact magnetically with the paramagnetic beads within the third droplet and initiate movement of the paramagnetic beads from the third droplet.

BRIEF DESCRIPTION OF THE DRAWINGS

The drawings furnished herewith illustrate a preferred methodology of the present invention in which the above advantages and features are clearly disclosed as well as others which will be readily understood from the following description of the illustrated embodiment.

In the drawings.

DETAILED DESCRIPTION OF THE DRAWINGS

Exclusive liquid repellency (ELR) is a phenomenon observed in solid-liquid-liquid three phase systems, where a solid surface shows complete repellency to a liquid (with a contact angle (CA)=180°) when exposed to a second liquid. This phenomenon is observed when a particular thermodynamic boundary condition is satisfied, for example, by the equation:

$$\gamma S/Lcp + \gamma Ldp/Lcp \leq \gamma S/Ldp \qquad \text{Equation (1)}$$

wherein: $\gamma$ is the interfacial tension; S is solid; Lcp is a liquid of continuous phase; and Ldp is a liquid of dispersed phase. As hereinafter described, ELR enables additional fluidic control in open aqueous fluid under oil provided for in the system of the present invention.

Figure 1:
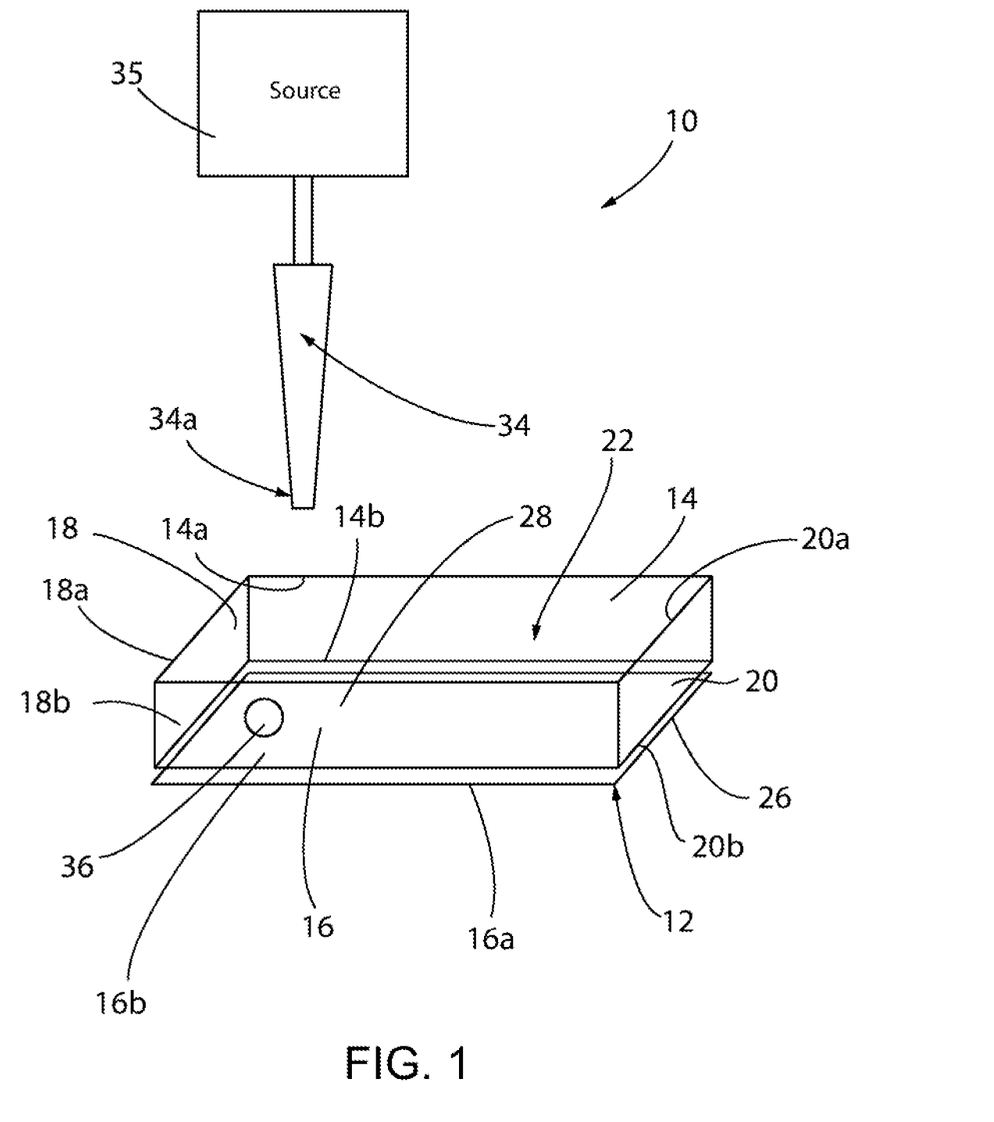
FIG. 1 is a schematic view of a system for effectuating the methodologies for volume-free reagent addition and exclusion-based sample preparation for streamlined multi-step assays.

Referring to FIG. 1, a schematic drawing depicting a system for carrying out a first aspect of the methodology of the present invention is generally designated by the reference numeral 10. System 10 includes microfluidic device 12 defined by first and second generally parallel, spaced side walls 14 and 16 respectively, interconnected by first and second generally parallel, spaced end walls 18 and 20, respectively. First and second side walls 14 and 16 respectively, and first and second end walls 18 and 20, respectively, define reservoir 22 for receiving a fluid, such as oil 24 or like, for reasons hereinafter described. Upper edges 14a and 16a of first and second side walls 14 and 16 respectively, and upper edges 18a and 20a of end walls 18 and 20, respectively, define an opening 26 for allowing access to reservoir 22. Lower edges 14b and 16b of first and second side walls 14 and 16 respectively, and lower edges 18b and 20b of end walls 18 and 20, respectively, are interconnected by an exclusive liquid repellency (ELR) surface 28 which communicates with reservoir 22. ELR surface 28 is a hydrophobic solid surface having specific surface chemical and physical conditions when in combination with a given oil phase 24 can repel aqueous solutions, as hereinafter described. It can appreciated that while microfluidic device 10 has a generally rectangular, box-like configuration, other configurations are possible without deviating from the scope of the present invention.

Figure 2:
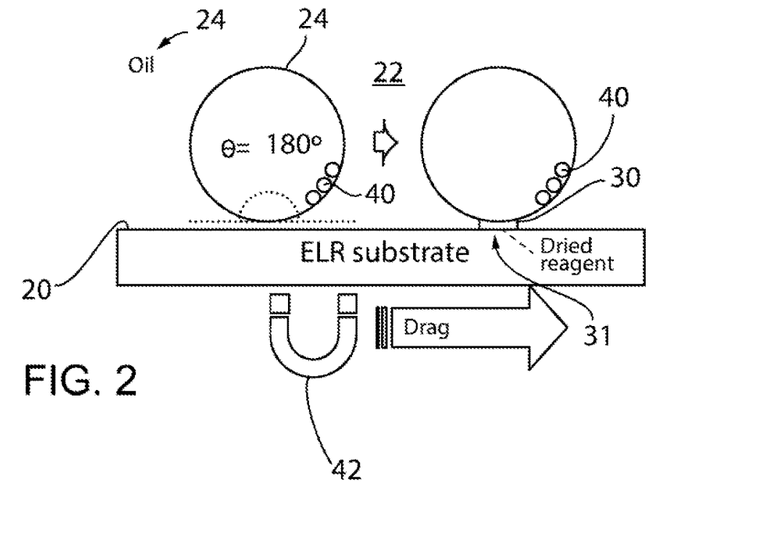
FIG. 2 is a schematic, side elevational view of the system of FIG. 1 depicting a first arrangement thereof wherein the system is used in the volume-free addition of a reagent to a sample.

It is contemplated for system 10 to be used in the volume-free addition of a reagent to a sample, FIG. 2. More specifically, with reservoir 22 dry and free of fluids, reagent 30 of interest in solution may be deposited onto ELR surface 28. Reagent 30 is allowed to dry (such as by desiccation and/or lyophilization) and physically adsorb onto ELR surface 28. It is contemplated to dry reagent 30 at a known location 31 or locations along ELR surface 28 in order to facilitate operation of microfluidic device 12 and/or integration of microfluidic device 12 with various liquid/fluid handling equipment. Once reagent 30 is dried on ELR surface 28, reservoir 22 of microfluidic device 12 is filled with a selected fluid, such as oil 24.

Injector 34, FIG. 1, is operatively connected to a source 35 and is configured to deliver droplet 36 of an aqueous solution of interest in oil 24 in reservoir 22 of microfluidic device 12 at a desired location. It is intended for the aqueous solution from which droplet 36 is formed to be immiscible with oil 24 in reservoir 22. Injector 34 may be configured to deliver droplet 36 of the aqueous solution directly into oil 24 (in other words, tip 34a of injector 34 may be submerged within oil 24). Alternatively, injector 34 may be configured to deliver droplet 36 by releasing droplet 36 above oil 34 and allowing gravity to bring droplet 36 into reservoir 22. This arrangement is only suitable for conditions where droplet 36 is sufficiently dense relative to oil 24 and a person having ordinary skill in the art could determine the conditions under which this is achievable either by computational methods or by routine experimental optimization. In either instance described above with respect to the injector 34, injector 34 may include a mechanism for urging droplet 36 out of tip 34a of injector 34. For example, such mechanism may include a plunger mechanism, a pump mechanism, such as a peristaltic pump, and the like. A computer (not shown) may be coupled to injector 34 and configured to control the introduction of droplet 36 into oil 24.

It is contemplated for droplet 36 to include paramagnetic beads 40 and for system 10 to include magnetic manipulator 42 configured to interact magnetically with paramagnetic beads 40 within droplet 36 to initiate movement of the droplet 36 within oil 24. Magnetic manipulator 42 can be handheld or can be coupled to an automated movement mechanism (not shown). The automated movement mechanism may be operatively connected to a computer (not shown) configured to control magnetic properties of the magnetic manipulator 42 and/or to control the optional automated movement mechanism associated with magnetic manipulator 42. By way of example, magnetic manipulator 42 may take the form of a magnet, an electromagnetic force generator, or the like.

Initially, magnetic manipulator 42 is utilized to draw droplet 36 over location 31 of the previously dried-up reagent 30 using magnetic manipulator 42. With droplet 36 positioned over location 31 of the previously dried-up reagent 30, droplet 36 picks-up and re-dissolves the desiccated reagent 30, with virtually no increase in the total volume of droplet 36. This phenomenon is possible due to the highly aqueous-repellent characteristic of ELR surface 28 under oil 24, which allows near complete recovery of the dried-up reagent by the aqueous droplet 36.

It can be understood that prior to depositing oil 24 in reservoir 22, a plurality of different reagents of interest in solution may be deposited onto ELR surface 28 and be allowed to dry and physically adsorb onto ELR surface 28 at known, corresponding locations. With the plurality of reagents dried on ELR surface 28, droplet 36 may be sequentially drawn to each of the known locations by magnetic manipulator 42, e.g. manually or by means of an automated movement mechanism, thereby enabling the multi-step addition of the plurality of different reagents via the sequentially dragging of droplet 36 along ELR surface 28 without adding to the total volume of droplet 36. It is contemplated to provide indicia along or adjacent to ELR surface 28 to allow an individual or the automated movement mechanism to accurately identify the known locations of the plurality of reagents dried on ELR surface 28.

Figure 3:
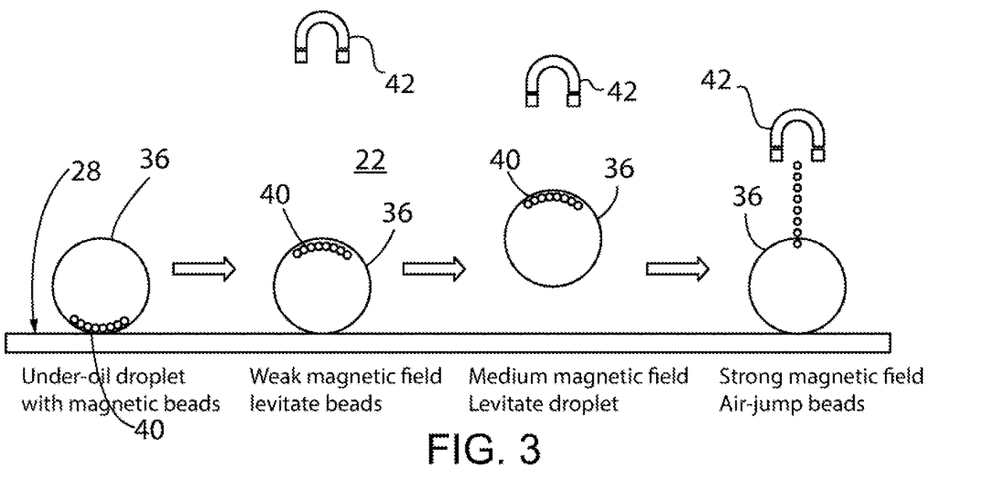
FIG. 3 is a schematic, side elevational view of the system of FIG. 1 depicting contact-free manipulation of a droplet having paramagnetic beads therein.

Referring to FIG. 3, it is contemplated for paramagnetic beads 40 within droplet 36 to be employed to enhance and mix the plurality of reagents within droplet 36 by moving magnetic manipulator 42 is a desired pattern, for example, by moving magnetic manipulator 42 up and down. It is further contemplated by manipulating the distance between magnetic manipulator 42 and paramagnetic beads 40, various droplet/bead manipulations can be performed, including sideways movement of droplet 36 within reservoir 22, the internal mixing of droplet 36, and the levitation of droplet 36 within reservoir 22. In addition, by increasing the magnetic force on paramagnetic beads 40 in droplet 36, for example, by moving magnetic manipulator 42 closer to droplet 36, paramagnetic beads 40 "jump" out of droplet 36 entirely. This, in turn, enables the recovery of analytes bound to paramagnetic beads 40. With paramagnetic beads 40 removed from droplet 36, droplet 36 is rendered inactive from further magnetic manipulation.

Figure 4:
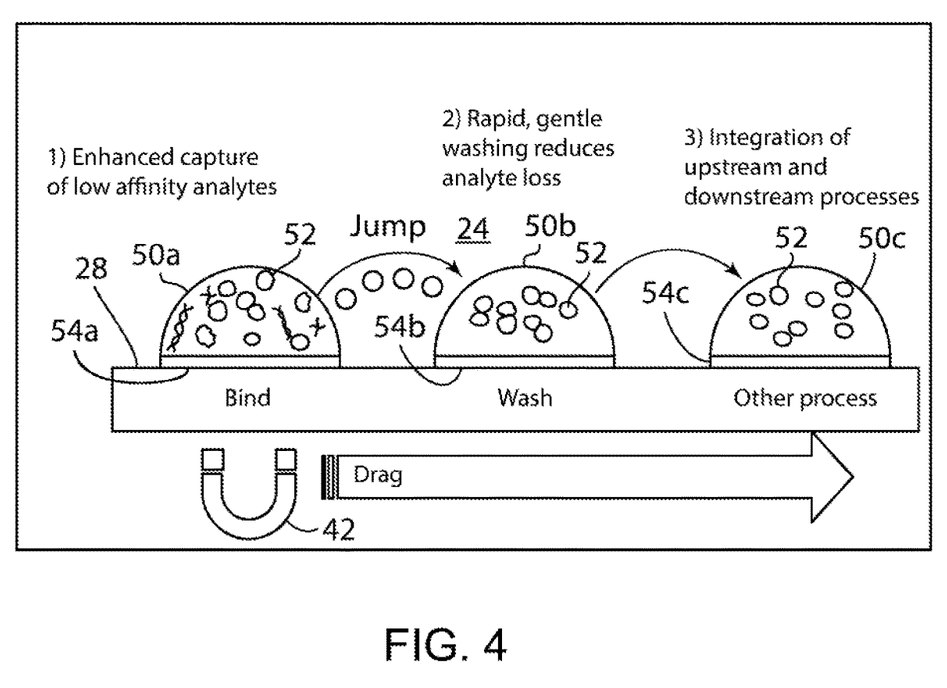
FIG. 4 is a schematic, side elevational view of the system of FIG. 1 depicting a second arrangement thereof wherein the system is used to perform exclusion-based sample preparation.

System 10 may also be used for effectuating a methodology for exclusion-based sample preparation (ESP), FIG. 4. More specifically, it is contemplated to utilize system 10 to perform sequential liquid exchanges by dragging functionalized paramagnetic beads 52 using a magnetic force generated by magnetic manipulator 42 from an aqueous phase through an immiscible oil barrier to fully "exclude" non-target analytes and into another aqueous phase to perform a rapid and single-step liquid exchange.

An array of hydrophilic spots 54a-54c are pre-patterned on ELR surface 28 of microfluidic device 12. As heretofore described, ELR surface 28 is a hydrophobic solid surface having specific surface chemical and physical conditions intended to repel aqueous solutions. One or move injectors 34 is configured to deliver a series of droplets 50a-50c of selected compositions on corresponding hydrophilic spots 54a-54c, respectively, on ELR surface 28. For example, droplet 50a may be composed of an aqueous solution having a desired analyte and functionalized paramagnetic beads 52 to which the desired analyte binds dispersed therein. Droplet 50b may be composed of a buffer solution for washing away unbound analyte with the minimal loss of any analytes bound to the functionalized paramagnetic beads 52. Droplet 50c may be composed of a still further solution, such as an elution solution, to wash away any proteins unbound to functionalized paramagnetic beads 52. It is also noted that a dried reagent (such as an immunoprecipitation (IP) buffer, an antibody, a low salt wash buffer, a high salt wash buffer, an elution buffer, a wash buffer, etc.), as heretofore described, may be provided on hydrophilic spots 54a-54c.

As such, a user need only deposit a droplet thereon to reconstitute the dried reagents. This arrangement allows microfluidic device 12 to be packaged as a single platform that includes all the necessary reagents to perform a desired assay. In either arrangement, it can be appreciated that the hydrophilic nature of the array of hydrophilic spots 54a-54c on ELR surface 28 acts to pin droplets 50a-50c thereon. In addition, the hydrophobic nature of ELR surface 28 further acts to retain droplets 50a-50c on hydrophilic spots 54a-54c of ELR surface 28.

Once droplets 50a-50c are deposited on corresponding hydrophilic spots 54a-54c, respectively, on ELR surface 28, magnetic manipulator 42 is positioned below ELR surface 28 such that a magnetic force generated by magnetic manipulator 42 magnetically attracts functionalized paramagnetic beads 52. More specifically, magnetic manipulator 42 is positioned below hydrophilic spot 50a of ELR surface 28 such that the magnetic force generated by magnetic manipulator 42 attracts the analyte-bound functionalized paramagnetic beads 52 in droplet 50a. Thereafter, as magnetic manipulator 42 is slid axially along the underside of ELR surface 28 to a position below hydrophilic spot 50b of ELR surface 28, the magnetic force generated by magnetic manipulator 42 draws the analyte-bound functionalized paramagnetic beads 52 from droplet 50a, through oil 24, and into droplet 50b. Due to the immiscible characteristics of oil 24 and aqueous phase of droplet 50a, the aqueous liquid may be removed from analyte-bound functionalized paramagnetic beads 52, thereby greatly reducing the residual liquid adsorbed on analyte-bound functionalized paramagnetic beads 52. With analyte-bound functionalized paramagnetic beads 52 received in droplet 50b, the buffer solution comprising droplet 50b washes away any unbound analyte with the minimal loss of the analytes bound to analyte-bound functionalized paramagnetic beads 52.

Once analyte-bound functionalized paramagnetic beads 52 is washed in droplet 50b, magnetic manipulator 42 may be slid axially along the underside of ELR surface 28 from a position below hydrophilic spot 50b of ELR surface 28 to a position below hydrophilic spot 50c of ELR surface 28, thereby drawing the analyte-bound functionalized paramagnetic beads 52 from droplet 50b, through oil 24, and into droplet 50c. Again, due to the immiscible characteristics of oil 24 and aqueous phase of droplet 50b, the aqueous liquid may be removed from analyte-bound functionalized paramagnetic beads 52, thereby greatly reducing the residual liquid adsorbed on analyte-bound functionalized paramagnetic beads 52. With analyte-bound functionalized paramagnetic beads 52 received in droplet 50c, the elution solution comprising droplet 50c washes away any proteins unbound to analyte-bound functionalized paramagnetic beads 52. Once analyte-bound functionalized paramagnetic beads 52 are washed in droplet 50c, analyte-bound functionalized paramagnetic beads 52 may be removed from droplet 50c by a magnetic force generated by magnetic manipulator 42 for further downstream processing. Alternatively, a magnetic force generated by magnetic manipulator 42 may be used to draw the analyte-bound functionalized paramagnetic beads 52 from droplet 50c, through oil 24, and into a downstream droplet (not shown) for further processing.

As described, the methodology for ESP heretofore described is inherently non-dilutive and more rapid than traditional techniques, thereby enabling higher analyte recovery and reduced sample loss. This, in turn, helps preserve molecular interactions between the desired analytes and the functionalized paramagnetic beads to which the desired analytes bind that are low affinity (high dissociation constant, Kd) or short lived (high interaction off-rate). Further, the functionalized paramagnetic beads may be moved from any given droplet to another in both the x and y directions, thereby allowing for more degrees of freedom of movement for the functionalized paramagnetic beads. It is further noted that the hydrophobic nature of ELR surface 28 ensures that very little, if any, residual liquid is left behind on the functionalized paramagnetic beads as the functionalized paramagnetic beads are moved between droplets and prevents "invasion" or cross contamination between droplets when the functionalized paramagnetic beads are moved therebetween.

As hereinafter described, system 10 and the methodologies heretofore described may be used to effectuate various multi-step assays. By way of example, system 10 and the methodologies heretofore described may be used for: 1) methylated-DNA (meDNA) extraction from rare samples; 2) antimicrobial susceptibility testing; and 3) extraction of chromatin-bound DNA from cells or tissues.

Figure 5:
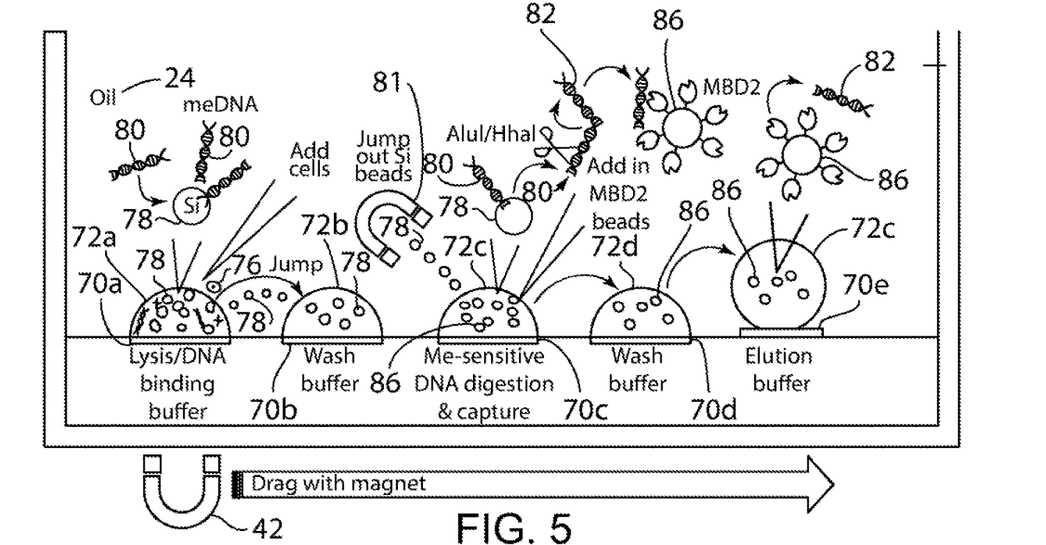
FIG. 5 is a schematic, side elevational view of the system of FIG. 1 depicting a third arrangement thereof wherein the system is used for the extraction of methylated-DNA (meDNA) from rare samples.

Referring to FIG. 5, selective oxygen (02) plasma may be used to etch ELR surface 28 to create regions 70a-70e of selective aqueous adhesion surrounded by ELR surface 28 that resist aqueous contact. Thereafter, reservoir 22 of microfluidic device 12 is filled with a selected fluid, such as oil 24. After flooding the reservoir 22 with oil 24, one or more injectors 34 are configured to deliver droplets 72a-72e of desired aqueous solutions in oil 24 in reservoir 22 of microfluidic device 12 to corresponding regions 70a-70e, respectively. It is intended for the aqueous solutions to be immiscible with oil 24 in reservoir 22. More specifically, droplet 72a may be composed of a lysis/DNA binding buffer; droplet 72b may be composed of a wash buffer; droplet 70c may be composed of a methylated-sensitive DNA digestion & capture solution; droplet 70d may be composed of a wash buffer; and droplet 72e may be composed elution buffer. As noted, the hydrophilic nature of regions 70a-70e on ELR surface 28 acts to pin droplets 72a-72e thereon. In addition, the hydrophobic nature of ELR surface 28 further acts to retain droplets 72a-72e on regions 70a-70e of ELR surface 28.

Cells 76 are isolated into droplet 72a and then lysed in situ by the lysis/DNA binding buffer thereby solubilizing DNA 80 of cells 76. Functionalized paramagnetic beads 78 are added to droplet 72a such that DNA 80 bind thereto. Thereafter, magnetic manipulator 42 is positioned below region 70a of ELR surface 28 such that the magnetic force generated by magnetic manipulator 42 attracts the DNA-bound functionalized paramagnetic beads 78 in droplet 72a. Magnetic manipulator 42 is slid axially along the underside of ELR surface 28 to a position below region 70b of ELR surface 28 such that the magnetic force generated by magnetic manipulator 42 draws the DNA-bound functionalized paramagnetic beads 78 from droplet 70a, through oil 24, and into droplet 70b. Due to the immiscible characteristics of oil 24 and aqueous phase of droplet 70a, the aqueous liquid is removed from DNA-bound functionalized paramagnetic beads 78, thereby greatly reducing the residual liquid adsorbed on DNA-bound functionalized paramagnetic beads 78. With DNA-bound functionalized paramagnetic beads 78 received in droplet 70b, wash buffer solution of droplet 70b washes away any undesired material from DNA-bound functionalized paramagnetic beads 78 with the minimal loss of the DNA bound to DNA-bound functionalized paramagnetic beads 78.

Magnetic manipulator 42 is then slid axially along the underside of ELR surface 28 to a position below region 70c of ELR surface 28, the magnetic force generated by magnetic manipulator 42 draws DNA-bound functionalized paramagnetic beads 78 from droplet 70b, through oil 24, and into droplet 70c. Due to the immiscible characteristics of oil 24 and aqueous phase of droplet 70b, the aqueous liquid is removed from DNA-bound functionalized paramagnetic beads 78, thereby greatly reducing the residual liquid adsorbed on DNA-bound functionalized paramagnetic beads 78.

In order to ensure system 10 is sensitive enough to pull out meDNA against a large amount of background unmethylated DNA, two restriction enzymes, AluI and HhaI, are added to droplet 70c. AluI is intended to fragment DNA 80 bound to functionalized paramagnetic beads 78 and HhaI is intended to further digest DNA 80 only at unmethylated restriction recognition sites, thereby preserving meDNA fragments 82. Once DNA 80 bound to functionalized paramagnetic beads 78 is fragmented and digested at the unmethylated restriction recognized sites, functionalized paramagnetic beads 78 may be drawn from droplet 70c by means of a secondary magnetic source, such as magnet 81. Separately, paramagnetic beads are coupled with the methyl-CpG binding domain of methyl-CpG binding domain protein 2 (MBD2-MBD) via His-tag chemistry to form MBD2-MBD conjugated paramagnetic beads 86. As is known, methyl-DNA binding (MBD) proteins, such as MBD2 enable the isolation of meDNA after restriction enzyme-based digestion of total DNA. Paramagnetic beads 86 are introduced into droplet 70c and mixed with meDNA fragments 80 so to allow the MBD2-MBD protein coupled to paramagnetic beads 86 to bind to meDNA fragments 82 within droplet 70c.

With meDNA fragments 82 bound to functionalized paramagnetic beads 86 in droplet 70c, magnetic manipulator 42 is, once again, slid axially along the underside of ELR surface 28 to a position below region 70d of ELR surface 28 such that the magnetic force generated by magnetic manipulator 42 draws the functionalized paramagnetic beads 86 from droplet 70c, through oil 24, and into droplet 70d. Due to the immiscible characteristics of oil 24 and aqueous phase of droplet 70c, the aqueous liquid is removed from functionalized paramagnetic beads 86, thereby greatly reducing the residual liquid adsorbed on functionalized paramagnetic beads 86. With functionalized paramagnetic beads 78 received in droplet 70d, wash buffer solution of droplet 70d washes away any undesired material from functionalized paramagnetic beads 86 with the minimal loss of meDNA fragments 82 bound to functionalized paramagnetic beads 86.

Once functionalized paramagnetic beads 86 are washed in droplet 70d, magnetic manipulator 42 is then slid axially along the underside of ELR surface 28 to a position below region 70e of ELR surface 28. The magnetic force generated by magnetic manipulator 42 draws functionalized paramagnetic beads 86 from droplet 70d, through oil 24, and into droplet 70e. Due to the immiscible characteristics of oil 24 and aqueous phase of droplet 70d, the aqueous liquid is removed from functionalized paramagnetic beads 86, thereby greatly reducing the residual liquid adsorbed on functionalized paramagnetic beads 86. Elution buffer of droplet 72e facilitates the elution of meDNA fragments 82 from functionalized paramagnetic beads 86. Functionalized paramagnetic beads 86 may be removed from droplet 72e by a magnetic force generated by a secondary magnetic force generator, e.g., a magnet (not shown), and transferred to a PCR tube (not shown), wherein functionalized paramagnetic beads 86 may be heated to a predetermined temperature (e.g., 95° C.) to cause elution of meDNA fragments 82 therefrom.

As described, by systematically arranging the sequence of the patterned hydrophilic spots on ELR surface 28, one can perform a streamlined reagent addition (lysis buffer), digestion (restriction enzymes), and extraction (capture by MBD2-modified paramagnetic beads) protocol by moving a magnet, without pipetting/liquid handling steps therebetween. The delivery of single cell lysis buffer into the droplets allows for the assay volume to remain low throughout the protocol to minimize analyte dilution and maximize recovery and binding.

To optimize the methodology of the present invention, it can be appreciated that routine alterations to the protocol as described above can be made. Such alterations may include: 1) Adjustments to the incubation times for cell lysis, the binding of the DNA and/or the DNA fragments to the functional paramagnetic beads, or restriction enzyme digestion to optimize the amount and purity of the output. Decreasing incubation times may reduce the amount of degradation of DNA or methylation signatures during the protocol. 2) Altering the magnetic bead chemistries for meDNA enrichment to increase meDNA recovery or purity. 3) Altering formulation of the elution buffers due to low sample yield.

With this method, detection of LINE1 meDNA from 0.006 ng of input human genomic DNA equivalent to approximately 1 cell is possible. Using LINE1 and GSTP1 methylation in cell lines as a model system, GSTP1 methylation in LNCaP prostate cancer cells may be detected, with little to no GSTP1 methylation signal from RWPE1 (which is normally non-methylated for GSTP1), FIG. 8. To test the ability to probe other epigenomic regions, meDNA enrichment was measured at HLA-A, HLA-B, and HLA-C in cancer cell lines where the RNA and protein expression is downregulated relative to noncancerous cell lines. As predicted, meDNA in cell lines with absent protein expression of HLA molecules (LAPC4, 22RV1 and LNCaP prostate cancer cell lines) was detected, but not in normal cells with high expression of HLA (including white blood cells, RWPE1-normal prostate epithelial cells, and LCL lymphoid cells). To test the ability to detect meDNA in patient samples, meDNA enrichment was measured at HLA-A, HLA-B, and HLA-C in matched human prostate tumor biopsies, FIG. 9, meDNA was detected at each of these loci in some patient biopsies, with meHLA-B detection in 5/5 samples tested, thus confirming the feasibility and potential clinical relevance of the methodology of the present invention.

Figure 6:
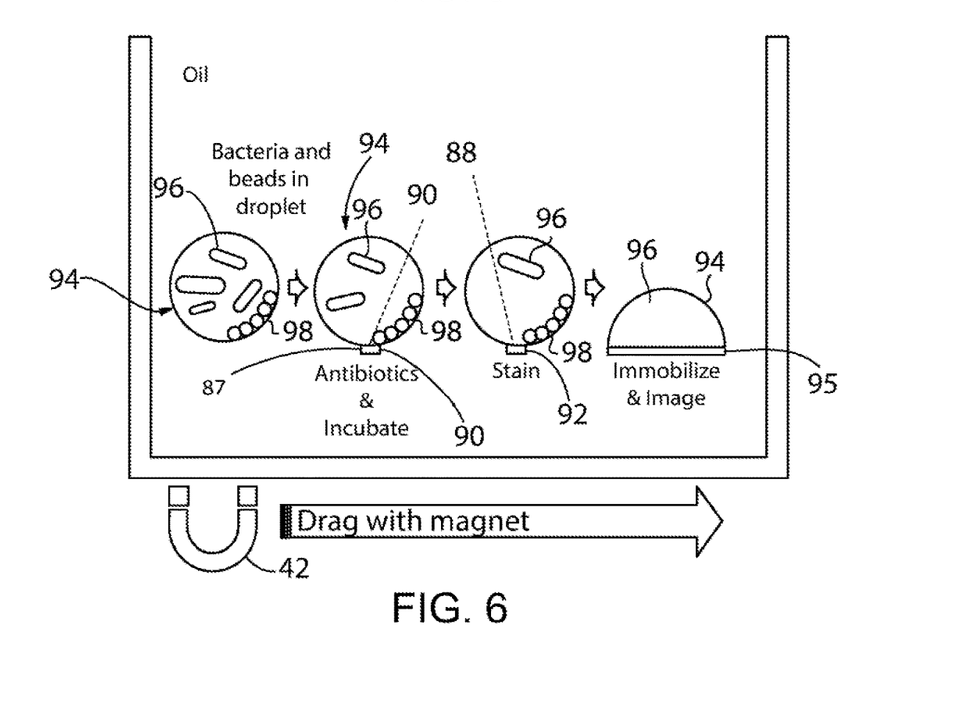
FIG. 6 is a schematic, side elevational view of the system of FIG. 1 depicting a fourth arrangement thereof wherein the system is used for antimicrobial susceptibility testing.

Referring to FIG. 6, it can be understood that system 10 may also be used to test for antimicrobial susceptibility. More specifically, with reservoir 22 dry and free of fluids, an antibiotic of interest 87 in solution may be deposited onto ELR surface 28 at a first location 90 and allowed to dry and physically adsorb onto ELR surface 28. In addition, a fluorescent bacteria stain 88 in solution may be deposited onto ELR surface 28 at a second location 92 and allowed to dry and physically adsorb onto ELR surface 28. Once the antibiotic of interest and the fluorescent bacteria stain are dried on ELR surface 28, reservoir 22 of microfluidic device 12 is filled with a selected fluid, such as oil 24.

In operation, injector 34 delivers droplet 94 of a desired volume, e.g., 2 µL, containing bacteria 96 and paramagnetic beads 98 into reservoir 22. As heretofore described, magnetic manipulator 42 is configured to interact magnetically with paramagnetic beads 98 within droplet 94 to initiate movement of the droplet 94. As such, magnetic manipulator 42 may be utilized to draw droplet 94 over first location 90 of the previously dried antibiotic of interest. With droplet 94 positioned over location 90 of the previously dried antibiotic of interest, droplet 94 picks-up and re-dissolves the antibiotic of interest 87 over a desired incubation period, (e.g., 24 hours), with virtually no increase in the total volume of droplet 94. This phenomenon is possible due to the highly aqueous-repellent characteristic of ELR surface 28 under oil 24, which allows near complete recovery of the dried antibiotic of interest by the aqueous droplet.

After the incubation period, magnetic manipulator 42 is utilized to drag droplet 94 through oil 24 to second location 92, wherein the fluorescent bacteria stain was previously dried. With droplet 94 positioned over second location 92 of the previously dried fluorescent bacteria stain 88, droplet 94 picks-up and re-dissolves the fluorescent bacteria stain for a desired time period, with virtually no increase in the total volume of droplet 94. As is known, any viable bacterial cells in droplet 94 after exposure to the antibiotic of interest will be stained by fluorescent bacteria stain 88 and may be detected by fluorescent microscopy. Once the viable bacterial cells in droplet 94 are stained by the fluorescent bacteria stain, magnetic manipulator 42 may be utilized to drag droplet 94 through oil 24 to hydrophilic spot 95 to pre-patterned on ELR surface 28 so as to immobilize droplet 94 thereon. Thereafter, fluorescent imaging of droplet 94 may be performed so as to allow for detection of any viable bacterial cells therein.

Figure 8:
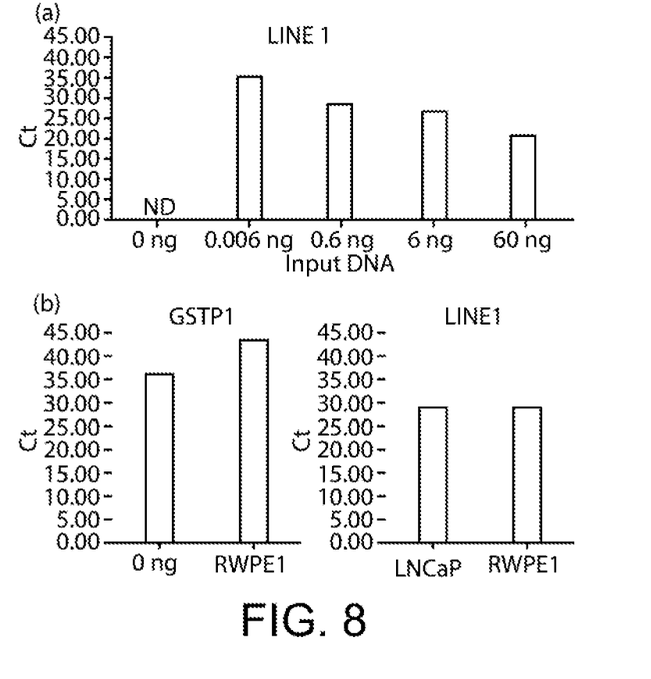
FIG. 8 are graphical charts showing (a) Ct values of extracted LINE1 meDNA from LNCaP cells with varying amounts of input DNA; and (b) Ct values of GSTP1 and LINE1 extracted methylated DNA from LNCaP prostate cancer and RWPE1 normal prostate cell lines using 0.6 ng input DNA.
Figure 9:
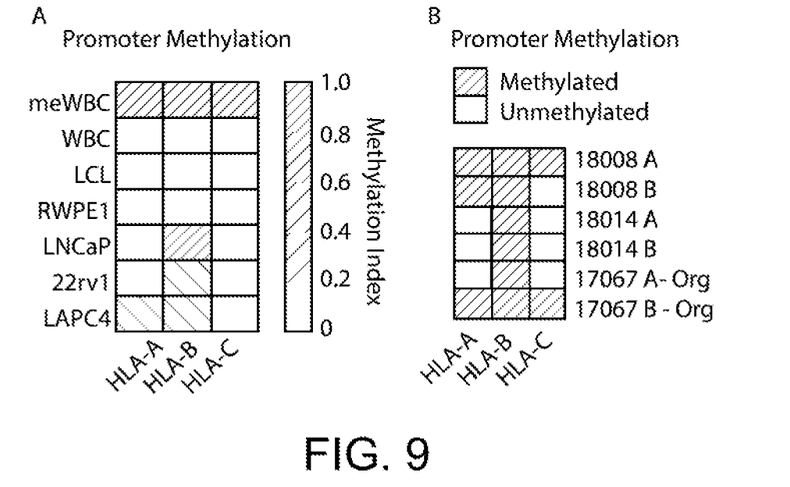
FIG. 9 are graphical charts showing (A) methylation status within the promoters of HLA-A, HLA-B, and HLA-C determined in cell lines and white blood cell (WBC) DNA wherein the methylation index is the ratio of methylated DNA in the enriched sample to methylated DNA in the same amount of input enzymatically methylated WBC DNA (meWBC) and a methylation index of 1.0 indicates methylation at every gene copy; (B) methylation status within the promoters of HLA-A, HLA-B, and HLA-C determined in biopsies from primary prostate cancer wherein two tumor sites were sampled from each patient, indicated as A or B following patient number, and Org: organoid grown from tumor cells obtained from biopsy.

Referring to FIG. 8, it is further contemplated to utilize system 10 to extract chromatin-bound DNA from cells or tissues. More specifically, with reservoir 22 dry and free of fluids, a nuclear isolation buffer is deposited onto ELR surface 28 at a first location 102 and allowed to dry and physically adsorb onto ELR surface 28. In addition, a micrococcal nuclease (MNase) digestion solution is deposited onto ELR surface 28 at a second location 104 and allowed to dry and physically adsorb onto ELR surface 28. A buffer such as a ethylenediaminetetraacetic acid (EDTA)/TRITON™ surfactant/deoxycholate solution is deposited onto ELR surface 28 at a third location 106 and allowed to dry and physically adsorb onto ELR surface 28.

Figure 7:
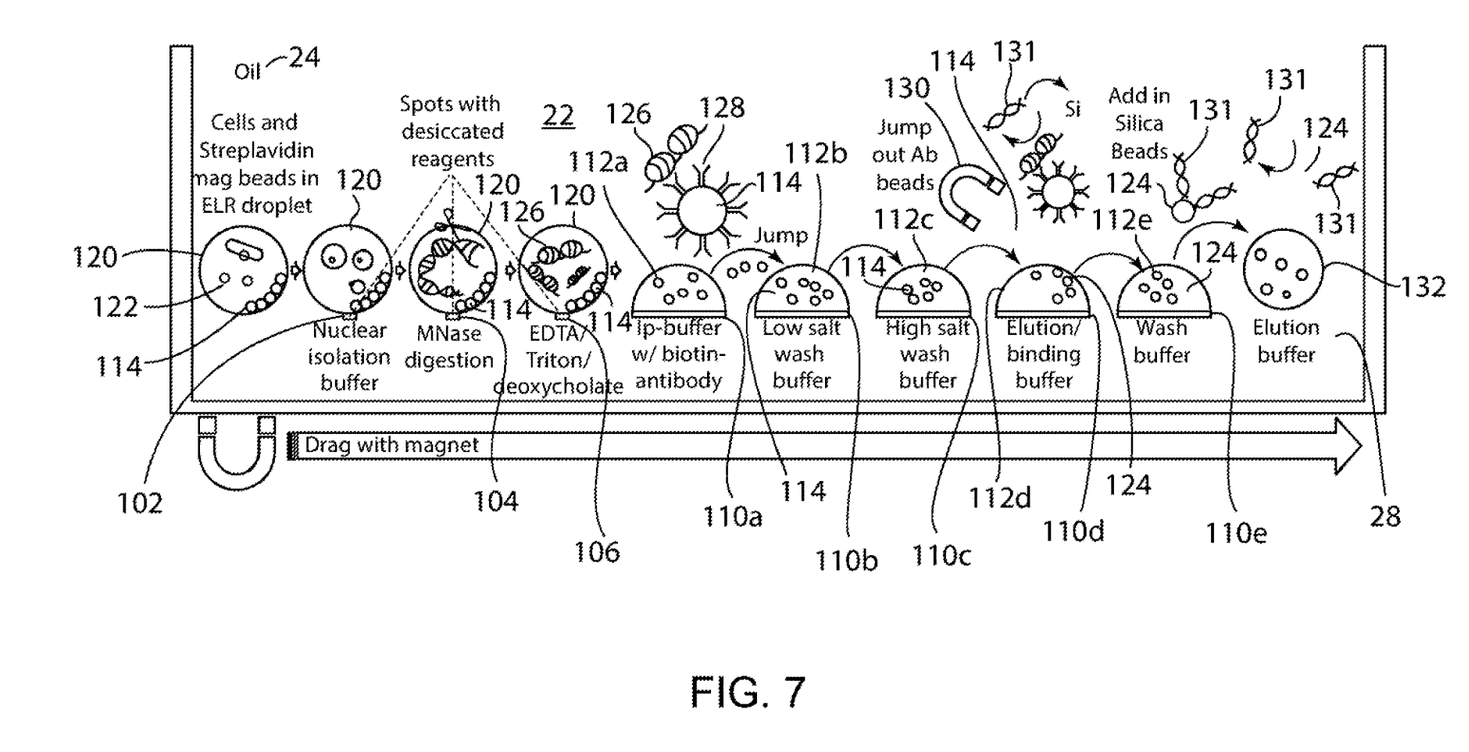
FIG. 7 is a schematic, side elevational view of the system of FIG. 1 depicting a fifth arrangement thereof wherein the system is used for extraction of chromatin-bound DNA from cells or tissues.

In addition, an array of hydrophilic spots 110a-110e are pre-patterned on ELR surface 28 of microfluidic device 12. It is intended for one or more injectors 34 to be configured to deliver a series of droplets 112a-112e of selected compositions on corresponding hydrophilic spots 110a-110c, respectively, on ELR surface 28. For example, droplet 110a may be composed of immunoprecipitation (IP) buffer containing biotinylated antibodies for facilitating the antibody-mediated capture of chromatin. Droplet 112b may be composed of a low salt wash buffer solution for washing away unbound reagents with the minimal loss of any chromatin bound to streptavidin paramagnetic beads 114, as hereinafter described. Droplet 112c may be composed of a high salt wash buffer solution for washing away unbound reagents with the minimal loss of any chromatin bound to the streptavidin paramagnetic beads 114. Droplet 112d may be composed of an elution/binding solution for eluting the DNA fragment of interest from the chromatin bound to streptavidin paramagnetic beads 114. Droplet 112e may be composed of a wash buffer solution for washing away unbound reagents with the minimal loss of any DNA fragments of interest from functionalized paramagnetic beads 124. It can be appreciated that the hydrophilic nature of the array of hydrophilic spots 110a-111e on ELR surface 28 act to pin droplets 112a-112e thereon. In addition, the hydrophobic nature of ELR surface 28 further acts to retain droplets 112a-112e on hydrophilic spots 110a-110e of ELR surface 28.

In operation, injector 34 delivers droplet 120 of a desired volume, e.g., 2 μL, containing cells 122 and streptavidin paramagnetic beads 14 into reservoir 22. As heretofore described, magnetic manipulator 42 is configured to interact magnetically with streptavidin paramagnetic beads 114 within droplet 120 to initiate movement of the droplet 120. As such, magnetic manipulator 42 may be utilized to draw droplet 120 over first location 102 of the previously dried nuclear isolation buffer. With droplet 120 positioned over first location 102 of the previously dried nuclear isolation buffer, droplet 120 picks-up and re-dissolves the nuclear isolation buffer over a desired incubation period, with virtually no increase in the total volume of droplet 120. By exposing cells 122 to the nuclear isolation buffer, the nuclear fraction of cells 122 are isolated.

Once the nuclear fractions of cells 122 are isolated, magnetic manipulator 42 is utilized to draw droplet 120 over second location 104 of the previously dried MNase digestion solution. With droplet 120 positioned over second location 104 of the previously dried MNase digestion solution, droplet 120 picks-up and re-dissolves the MNase digestion solution over a desired incubation period, with virtually no increase in the total volume of droplet 120. The MNase digestion solution of droplet 120 fragments the chromatin complexes released from the nuclear fraction of cell lysates from cells 122.

After the chromatin are released from the nuclear fraction of cells 122 and chromatin 126 is sheared, magnetic manipulator 42 is utilized to draw droplet 120 over third location 106 of the previously dried EDTA/TRITON™ surfactant/deoxycholate solution. With droplet 120 positioned over third location 106 of the previously dried EDTA/TRITON™ surfactant/deoxycholate solution, droplet 120 picks-up and re-dissolves the EDTA/TRITON™ surfactant/deoxycholate solution over a desired incubation period, with virtually no increase in the total volume of droplet 120. The EDTA/TRITON™ surfactant/deoxycholate solution of droplet 120 facilitates the decellularization and solubilization of proteins contained in cells 122.

Magnetic manipulator 42 then draws droplet 120 over hydrophilic spot 110a such that droplet 120 communicates with and combines with droplet 112a. With droplet 120 and droplet 112a combined, biotinylated antibodies 128 bind to streptavidin paramagnetic beads 114 and to sheared chromatin 126. With chromatin 126 bound to streptavidin paramagnetic beads 114 (through biotinylated antibodies 128) in combined droplets 120 and 112a, magnetic manipulator 42 is, once again, slid axially along the underside of ELR surface 28 to a position below hydrophilic spot 110b such that the magnetic force generated by magnetic manipulator 42 draws streptavidin paramagnetic beads 114 from combined droplets 120 and 112a, through oil 24, and into droplet 112b. Due to the immiscible characteristics of oil 24 and aqueous phase of combined droplets 120 and 112a, the aqueous liquid is removed from streptavidin paramagnetic beads 114, thereby greatly reducing the residual liquid adsorbed on streptavidin paramagnetic beads 114. With streptavidin paramagnetic beads 114 received in droplet 112b, low salt wash buffer solution of droplet 112b washes away any undesired material from streptavidin paramagnetic beads 114 with the minimal loss of chromatin 126 bound to streptavidin paramagnetic beads 114.

After the initial washing in droplet 112b, magnetic manipulator 42 is slid axially along the underside of ELR surface 28 to a position below hydrophilic spot 110c such that the magnetic force generated by magnetic manipulator 42 draws streptavidin paramagnetic beads 114 from droplet 112b, through oil 24, and into droplet 112c. Due to the immiscible characteristics of oil 24 and aqueous phase of droplets 112b, the aqueous liquid is removed from streptavidin paramagnetic beads 114, thereby greatly reducing the residual liquid adsorbed on streptavidin paramagnetic beads 114. With streptavidin paramagnetic beads 114 received in droplet 112c, high salt wash buffer solution of droplet 112c further washes away any undesired material from streptavidin paramagnetic beads 114 with the minimal loss of chromatin 126 bound to streptavidin paramagnetic beads 114.

Once streptavidin paramagnetic beads 114 are washed in droplet 112c, magnetic manipulator 42 is slid axially along the underside of ELR surface 28 to a position below hydrophilic spot 110d of ELR surface 28. The magnetic force generated by magnetic manipulator 42 draws streptavidin paramagnetic beads 114 from droplet 112c, through oil 24, and into droplet 112d. Due to the immiscible characteristics of oil 24 and aqueous phase of droplet 112c, the aqueous liquid is removed from streptavidin paramagnetic beads 114, thereby greatly reducing the residual liquid adsorbed on streptavidin paramagnetic beads 114. Elution buffer of droplet 112d facilitates the elution of DNA 131 from chromatin 126 bound to streptavidin paramagnetic beads 114. Streptavidin paramagnetic beads 114 may be removed from droplet 112d by a magnetic force generated by a secondary magnetic force generator, e.g., magnet 130. Thereafter, functionalized paramagnetic beads 124 are introduced in droplet 112d. Functionalized paramagnetic beads 124 are coated with a material, e.g. silica, such that DNA 131 binds thereto.

Once DNA 131 binds to functionalized paramagnetic beads 124, magnetic manipulator 42 is slid axially along the underside of ELR surface 28 to a position below hydrophilic spot 110e such that the magnetic force generated by magnetic manipulator 42 draws functionalized paramagnetic beads 124 from droplet 112d, through oil 24, and into droplet 112e. Due to the immiscible characteristics of oil 24 and aqueous phase of droplet 112d, the aqueous liquid is removed from functionalized paramagnetic beads 124, thereby greatly reducing the residual liquid adsorbed on functionalized paramagnetic beads 124. With functionalized paramagnetic beads 124 received in droplet 12e, wash buffer solution of droplet 112e washes away any undesired material from functionalized paramagnetic beads 124 with the minimal loss of DNA 131 bound thereto.

After functionalized paramagnetic beads 124 are washed, injector 34 delivers droplet 132 of an elution buffer having a desired volume into reservoir 22. Magnetic manipulator 42 is slid axially along the underside of ELR surface 28 so as to draw functionalized paramagnetic beads 124 from droplet 112, through oil 24, and into droplet 132. Due to the immiscible characteristics of oil 24 and aqueous phase of droplet 112e, the aqueous liquid is removed from functionalized paramagnetic beads 124, thereby greatly reducing the residual liquid adsorbed on functionalized paramagnetic beads 124. Elution buffer of droplet 132 facilitates the elution of DNA 131 from functionalized paramagnetic beads 124. Once DNA 131 is eluded from functionalized paramagnetic beads 124, DNA 131 may be removed from droplet 132 for further downstream processing.

Various modes of carrying out the invention are contemplated as being within the scope of the following claims particularly pointing out and distinctly claiming the subject matter that is regarded as the invention.

We claim:

1. A method of sample preparation for streamlined multi-step assays, comprising the steps:
providing a microfluidic device including a reservoir defined by a surface;
providing a dried reagent on a portion of the surface;
filling the reservoir with an oil, the oil interacting with the surface so as to cause the surface to repel an aqueous solution; and
positioning a droplet of the aqueous solution within the oil on the dried reagent, the droplet picking-up and dissolving the dried reagent therein so as to expose the portion of the surface.

2. The method of claim 1 wherein the step of providing the dried reagent on the portion of the surface comprises the additional steps:
depositing the reagent on the surface; and
allowing reagent to dry and physically adsorb onto surface.

3. The method of claim 1 wherein the droplet includes paramagnetic beads therein.

4. The method of claim 3 wherein the step of positioning the droplet of the aqueous solution on the dried reagent includes the steps of:
generating a magnetic force; and
positioning the magnetic force interact magnetically with the paramagnetic beads within the droplet; and
moving the magnetic force to initiate corresponding movement of the droplet to the portion of the surface.

5. The method of claim 4 comprising the additional step of patterning a hydrophilic spot on the surface at a second location.

6. The method of claim 5 wherein the portion of the surface is a hydrophilic spot.

7. The method of claim 5 comprising the additional step of moving the droplet with the dissolved reagent to the hydrophilic spot.

8. The method of claim 7 wherein the droplet is pinned at the hydrophilic spot.

9. The method of claim 7 wherein the step of moving the droplet with the dissolved reagent to the hydrophilic spot includes the additional steps of:
positioning the magnetic force to interact magnetically with the paramagnetic beads within the droplet; and
moving the magnetic force to initiate corresponding movement of the droplet to the hydrophilic spot.

10. The method of claim 9 wherein the hydrophilic spot is a first hydrophilic spot and wherein the method comprises the additional step of patterning a second hydrophilic spot on the surface at a third location.

11. The method of claim 10 wherein the aqueous solution is a first aqueous solution and the droplet is a first droplet and wherein the method further comprises the additional step of pinning a second droplet of a second solution at the second hydrophilic spot.

12. The method of claim 11 further comprising the additional steps of:
positioning the magnetic force to interact magnetically with the paramagnetic beads within the first droplet; and
moving the magnetic force to initiate corresponding movement of the paramagnetic beads from the first droplet to the second droplet.

13. The method of claim 4 wherein the dried reagent is a first dried reagent and the portion of the surface is a first portion and wherein the method further comprises the additional step of providing a second dried reagent on a second portion of the surface.

14. The method of claim 13 wherein the step of providing the second dried reagent on the second portion of the surface comprises the additional steps:
   depositing the second reagent on the second portion of the surface; and
   allowing second reagent to dry and physically adsorb onto the second portion of the surface.

15. The method of claim 13 comprising the additional steps of:
   positioning the magnetic force interact magnetically with the paramagnetic beads within the droplet; and
   moving the magnetic force to initiate corresponding movement of the droplet to the second portion of the surface.

16. The method of claim 14 comprising the additional step of picking-up and re-dissolving the second dried reagent in the droplet so as to expose the second portion of the surface.

17. A method of sample preparation for streamlined multi-step assays, comprising the steps:
   providing a microfluidic device including a reservoir defined by a surface;
   patterning first and second hydrophilic spots at corresponding first and second locations of the surface;
   filling the reservoir with an oil, the oil interacting with the surface so as to cause the portions of the surface outside of the first and second locations to repel an aqueous solution;
   depositing a first droplet of a first aqueous solution within the oil on the first hydrophilic spot and a second droplet of a second aqueous solution within the oil on the second hydrophilic spot, the first droplet including paramagnetic beads;
   generating a magnetic force configured to interact magnetically with the paramagnetic beads within the first droplet; and
   moving the magnetic force to initiate corresponding movement of the paramagnetic beads from the first droplet, through the oil, into the second droplet.

18. The method of claim 17 further comprising the step of providing a dried reagent at a third location of the surface prior to filling the reservoir with oil.

19. The method of claim 18 wherein the step of providing the dried reagent at the third location of the surface comprises the additional steps:
   depositing the reagent in a third aqueous solution on the surface; and
   allowing the third aqueous solution to dry such that a dried reagent is physically adsorbed onto surface.

20. The method of claim 19 comprising the additional step of positioning a third droplet of a third aqueous solution on the dried reagent, the third droplet picking-up and re-dissolving the dried reagent therein so as to expose the portion of the surface.

21. The method of claim 20 wherein the paramagnetic beads are initially in the third droplet and wherein the method comprises the additional steps of:
   positioning the magnetic force to interact magnetically with the paramagnetic beads within the third droplet; and
   moving the magnetic force to initiate corresponding movement of the paramagnetic beads from the third droplet, through the oil, into the first droplet.

22. The method of claim 20 wherein the paramagnetic beads are initially in the third droplet and wherein the method comprises the additional steps of:
   positioning the magnetic force to interact magnetically with the paramagnetic beads within the third droplet; and
   moving the magnetic force to initiate corresponding movement of the third droplet into fluid communication with the first droplet.

23. The method of claim 20 comprising the additional steps of:
   positioning the magnetic force to interact magnetically with the paramagnetic beads within the second droplet; and
   moving the magnetic force to initiate corresponding movement of the paramagnetic beads from the second droplet, through the oil, into the third droplet.

24. The method of claim 23 comprising the additional step of
   positioning the magnetic force to interact magnetically with the paramagnetic beads within the third droplet; and
   causing the magnetic force to initiate movement of the paramagnetic beads from the third droplet.

25. The method of claim 17 wherein the first droplet is pinned at the first hydrophilic spot and the second droplet is pinned at the second hydrophilic spot.

26. The method of claim 17 comprising the additional steps of drying a first reagent on the first hydrophilic spot and drying the second reagent on the second hydrophilic spot.

* * * * *

UNITED STATES PATENT AND TRADEMARK OFFICE
CERTIFICATE OF CORRECTION

| | |
|---|---|
| PATENT NO. | : 11,618,021 B2 |
| APPLICATION NO. | : 16/912986 |
| DATED | : April 4, 2023 |
| INVENTOR(S) | : Beebe et al. |

It is certified that error appears in the above-identified patent and that said Letters Patent is hereby corrected as shown below:

In the Specification

Column 1, Line 15, should read:
-- This invention was made with government support under CA181648 awarded by the National Institutes of Health and under W81XWH-16-1-0514 awarded by the ARMY/MRDC. The government has certain rights in the invention. --

Signed and Sealed this
Eleventh Day of July, 2023

Katherine Kelly Vidal
*Director of the United States Patent and Trademark Office*